United States Patent [19]

Maeda et al.

[11] 4,077,968
[45] Mar. 7, 1978

[54] THIAZOLE DERIVATIVES

[75] Inventors: Ryozo Maeda, Osaka; Katsumi Hirose, Kishiwada, both of Japan

[73] Assignee: Shionogi & Co., Ltd., Osaka, Japan

[21] Appl. No.: 730,965

[22] Filed: Oct. 8, 1976

Related U.S. Application Data

[60] Division of Ser. No. 596,244, July 16, 1974, Pat. No. 4,025,528, which is a continuation-in-part of Ser. No. 516,867, Oct. 21, 1974, abandoned.

[30] Foreign Application Priority Data

Oct. 24, 1973  Japan ............................... 48-119573
Oct. 29, 1973  Japan ............................... 48-121534

[51] Int. Cl.$^2$ .................. A61K 31/38; C07D 277/34; C07D 277/36; C07D 277/42
[52] U.S. Cl. ..................... 260/306.8 R; 260/302 R; 260/299; 424/245; 424/270
[58] Field of Search .................... 260/302 R, 306.8 R, 260/299

[56] References Cited

U.S. PATENT DOCUMENTS 3,968,120  7/1976  Regel et al. .................... 260/299
4,005,083  1/1977  Büchel et al. .................... 260/309

Primary Examiner—Donald G. Daus
Assistant Examiner—James H. Turnipseed
Attorney, Agent, or Firm—Wenderoth, Lind & Ponack

[57] ABSTRACT

Thiazole derivatives represented by the general formula:

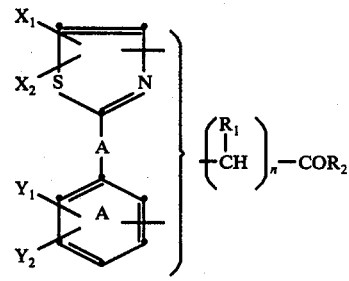

wherein A is oxygen, sulfur, imino, or $NR_3$, wherein $R_3$ is $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_1$ is hydrogen, $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_2$ is hydroxy, $C_{1-5}$ alkoxy or OM, wherein M is alkali metal, or one equivalent of alkaline earth metal, cupric or aluminum cation; $n$ is an integer of 0 or 1; $X_1$ and $X_2$ are independently hydrogen or $C_{1-5}$ alkyl; $Y_1$ and $Y_2$ are independently hydrogen, halogen, $C_{1-5}$ alkyl, $C_{1-5}$ alkoxy or trifluoromethyl; and the group

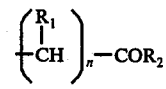

is linked to one of the meta or para positions of the benzene ring A, $n$ is not 0 when A is imino and —$CH_2$—$COR_2$ does not substitute the thiazole ring when A is imino, being useful as anti-inflammatory, anti-rheumatic, analgesic or anti-lipemia agents.

13 Claims, No Drawings

THIAZOLE DERIVATIVES

This application is a division of application Ser. No. 596,244, filed July 16, 1974, now U.S. Pat. No. 4,025,528 which application is in turn a continuation-in-part of application Ser. No. 516,867, filed Oct. 21, 1974 (now abandoned).

This invention provides novel thiazole derivatives and the salts. Further it relates to processes for their preparation.

The said thiazole derivatives and their pharmaceutically acceptable salts are represented by the general formula:

$$\begin{pmatrix} X_1 \\ X_2 \end{pmatrix} \begin{matrix} \\ S \end{matrix} \begin{matrix} \\ N \\ A \end{matrix} \begin{pmatrix} Y_1 \\ Y_2 \end{pmatrix} A \quad \Bigg\} - \begin{pmatrix} R_1 \\ | \\ CH \end{pmatrix}_n - COR_2 \qquad I$$

wherein

A is oxygen, sulfur, imino, or $NR_3$, wherein $R_3$ is $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl;

$R_1$ is hydrogen, $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl;

$R_2$ is hydroxy, $C_{1-5}$ alkoxy or OM, wherein M is alkali metal, or one equivalent of alkaline earth metal, cupric or aluminium cation;

n is an integer of 0 or 1;

$X_1$ and $X_2$ are independently hydrogen or $C_{1-5}$ alkyl;

$Y_1$ and $Y_2$ are independently hydrogen, halogen, $C_{1-5}$ alkyl, $C_{1-5}$ alkoxy or trifluoromethyl; and the group $$-\begin{pmatrix} R_1 \\ | \\ CH \end{pmatrix}_n - COR_2$$

is linked to one of the meta or para positions of the benzene ring A, n is not 0 when A is imino and $-CH_2COR_2$ does not substitute the thiazole ring when A is imino.

The term $C_{1-5}$ alkyl, as used herein, refers to both straight and branched aliphatic radicals of one to five carbon atoms including methyl, ethyl, propyl, i-propyl, butyl, i-butyl, t-butyl, pentyl, i-pentyl and the like. The term $C_{2-5}$ alkenyl refers to the aliphatic radicals of two to five carbon atoms with a double bond including vinyl, allyl, methallyl, 1-pentenyl, 2-isopentenyl and the like. The term $C_{3-5}$ alkynyl refers to the aliphatic radicals of three to five carbon atoms with a triple bond including 1-propynyl, 2-propynyl, 1-butynyl, 2-pentynyl and the like. The term $C_{3-6}$ cycloalkyl-$C_{1-3}$ alkyl refers to $C_{1-3}$ alkyl substituted by $C_{3-6}$ cycloalkyl including cyclopropyl, cyclobutyl, cyclopentyl and cyclohexyl. The term $C_{7-8}$ aralkyl refers to methyl or ethyl substituted by phenyl, i.e. benzyl and phenethyl. The term $C_{1-5}$ alkoxy refers to ether radicals of one to five carbon atoms as exemplified in the term $C_{1-5}$ alkyl. $C_{1-5}$ alkoxy is exemplified methoxy, ethoxy, propoxy, i-propoxy, butoxy, t-butoxy and pentoxy. Halogen includes chlorine, fluorine, bromine and iodine. Alkali metal refers to sodium, potassium and lithium. Alkaline earth metal refers to calcium, magnesium and barium. These definitions are used throughout the disclosure.

In the above general formula I, the group $$\begin{pmatrix} R_1 \\ | \\ CH \end{pmatrix}_n - COR_2$$

may be linked to one of the 4- or 5-positions of the thiazole ring or one of the meta or para positions of the benzene ring.

In the above general formula, the preferred n is 1. The preferred $X_1$ and $X_2$ are independently hydrogen and methyl. More preferably either of them is hydrogen. The preferred $Y_1$ and $Y_2$ are independently hydrogen, fluorine, chlorine and methyl. The preferred $R_1$ is hydrogen, methyl, ethyl, allyl, 2-methallyl, 2-propynyl, cyclopropyl-methyl and benzyl, more preferred is hydrogen and methyl, especially methyl. The preferred $R_2$ is hydroxy. The preferred $R_3$ is methyl, allyl, cyclopropyl-methyl and benzyl, especially methyl. The group $$\begin{pmatrix} R_1 \\ | \\ CH \end{pmatrix}_n - COR_2$$

is preferably linked to the para position of the benzene ring when the group is linked to the benzene ring A.

The said thiazole derivatives of formula I are novel and have excellent anti-inflammatory, anti-rheumatic and analgesic activities as well as anti-lipemia activity. They are useful in the treatment of inflammatory of lipemia diseases in man and warm-blooded animals. Further, carboxylic acid derivatives, the compounds of formula I of which n is 0, can be used as starting material of other compounds of the present invention.

In a particular aspect, the present invention provides novel compounds of the formula:

$$\begin{matrix} X_1 \\ \\ S \end{matrix} \begin{matrix} \\ \\ \\ O \end{matrix} \begin{pmatrix} R_1 \\ | \\ CH \end{pmatrix}_n - COR_2 \qquad I\text{-}1$$

$$\begin{matrix} Y_1 \\ \\ Y_2 \end{matrix} A$$

wherein $R_1$, $R_2$, n, $X_1$, $Y_1$ and $Y_2$ each has the same significance designated above.

Illustrative of these compounds represented by formula I-1 and presented as their free acid are the following:

2-phenoxy-4-thiazolecarboxylic acid,
2-phenoxy-5-thiazolecarboxylic acid,
2-phenoxy-5-methyl-4-thiazolecarboxylic acid,
2-phenoxy-5-ethyl-4-thiazolecarboxylic acid,
2-phenoxy-4-methyl-5-thiazolecarboxylic acid, 2-(4-chlorophenoxy)-4-thiazolecarboxylic acid,
2-(4-chlorophenoxy)-5-thiazolecarboxylic acid,
2-(4-chlorophenoxy)-5-methyl-4-thiazolecarboxylic acid,
2-(4-chlorophenoxy)-4-methyl-5-thiazolecarboxylic acid,
2-(4-methylphenoxy)-4-methyl-5-thiazolecarboxylic acid,
2-(3-trifluoromethylphenoxy)-4-methyl-5-thiazolecarboxylic acid,
2-(2,3-dimethylphenoxy)-4-methyl-5-thiazolecarboxylic acid,
2-(2-phenoxy-4-thiazolyl)acetic acid,
2-(2-phenoxy-4-methyl-5-thiazolyl)acetic acid,
2-(2-phenoxy-4-thiazolyl)propionic acid,
2-(2-phenoxy-5-thiazolyl)propionic acid,
2-(2-phenoxy-5-methyl-4-thiazolyl)propionic acid,
2-(2-phenoxy-4-methyl-5-thiazolyl)propionic acid,
2-(2-phenoxy-4-ethyl-5-thiazolyl)propionic acid,
2-[2-(4-chlorophenoxy)-4-thiazolyl]propionic acid,
2-[2-(3-ethylphenoxy)-5-thiazolyl]propionic acid,
2-[2-(4-chlorophenoxy)-5-thiazolyl]propionic acid,
2-[2-(2,4-dichlorophenoxy)-5-thiazolyl]propionic acid,
2-[2-(4-chlorophenoxy)-5-methyl-4-thiazolyl]propionic acid,
2-[2-(4-chlorophenoxy)-4-methyl-5-thiazolyl]propionic acid,
2-[2-(4-methylphenoxy)-4-methyl-5-thiazolyl]propionic acid,
2-[2-(3-trifluoromethylphenoxy)-4-methyl-5-thiazolyl]propionic acid,
2-[2-(2,3-dimethylphenoxy)-4-methyl-5-thiazolyl]propionic acid,
2-(2-phenoxy-4-thiazolyl)butyric acid,
2-(2-phenoxy-4-thiazolyl)-4-pentenic acid,
2-(2-phenoxy-5-thiazolyl)-3-cyclopropylpropionic acid,
2-(2-phenoxy-4-thiazolyl)-3-phenylpropionic acid, and the like.

The preferred compounds of formula I-1 are 2-(2-phenoxy-thiazolyl) acetic or propionic acids which may be substituted by methyl on the thiazole ring and one or two fluorines, chlorines or methyls on the benzene ring. The most preferred compounds are 2-(2-phenoxy-5-thiazolyl)propionic acid, 2-(2-phenoxy-4-methyl-5-thiazolyl)propionic acid and the metal salts.

In a further aspect, the invention provides novel compounds of the formula:

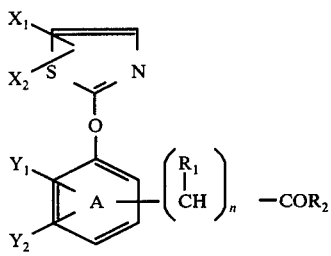

I-2 wherein $R_1$, $R_2$, $n$, $X_1$, $X_2$, $Y_1$ and $Y_2$ each has the same significance designated above, and the group

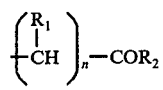

is linked to one of the meta or para positions of the benzene ring A.

Illustrative of these compounds represented by formula I-2 and presented as their free acid are the following:
4-(2-thiazolyloxy)benzoic acid,
2-chloro-3-methyl-4-(2-thiazolyloxy)benzoic acid,
3-fluoro-4-(2-thiazolyloxy)benzoic acid,
2-[4-(2-thiazolyloxy)phenyl]acetic acid,
2-[3-(2-thiazolyloxy)phenyl]propionic acid,
2-[4-(2-thiazolyloxy)phenyl]propionic acid,
2-[4-(4-methyl-2-thiazolyloxy)phenyl]propionic acid,
2-[3-fluoro-4-(2-thiazolyloxy)phenyl]propionic acid,
2-[3-(2-thiazolyloxy)-5-methylphenyl]propionic acid,
2-[2-chloro-3-methyl-4-(2-thiazolyloxy)phenyl]propionic acid,
2-[2-methyl-4-(2-thiazolyloxy)-5-chlorophenyl]propionic acid,
2-[3-(4-methy-2-thiazolyloxy)-5-chlorophenyl]propionic acid,
2-[3-(4-methyl-2-thiazolyloxy)-4-fluorophenyl]propionic acid,
2-[4-(4-methyl-2-thiazolyloxy)phenyl]propionic acid,
2-[4-(4,5-dimethyl-2-thiazolyloxy)phenyl]propionic acid,
2-[2-chloro-4-(2-thiazolyloxy)phenyl]propionic acid,
2-[3-chloro-4-(2-thiazolyloxy)phenyl]propionic acid,
2-[2-fluoro-4-(2-thiazolyloxy)phenyl]propionic acid,
2-[2-methyl-4-(2-thiazolyloxy)phenyl]propionic acid,
2-[3-methyl-4-(2-thiazolyloxy)phenyl]propionic acid,
2-[3-methoxy-4-(2-thiazolyloxy)phenyl]propionic acid,
2-[3-(2-thiazolyloxy)phenyl]butyric acid,
2-[4-(2-thiazolyloxy)phenyl]butyric acid,
2-[4-(2-thiazolyloxy)phenyl]-4-pentenoic acid,
2-[4-(2-thiazolyloxy)phenyl]-4-pentynoic acid,
2-[4-(2-thiazolyloxy)phenyl]-3-cyclopropylpropionic acid,
2-[4-(2-thiazolyloxy)phenyl]-4-methyl-4-pentenoic acid,
2-[3-(2-thiazolyloxy)phenyl]-3-phenylpropionic acid,
2-[4-(2-thiazolyloxy)phenyl]-3-phenylpropionic acid and the like.

The preferred compounds of formula I-2 are 2-[4-(2-thiazolyloxy)phenyl]propionic acids which may be substituted on the thiazole ring by methyl and on the benzene ring by one or two substituents selected from chlorine, fluorine and methyl. The corresponding acetic acid derivatives are also preferred. They are, for example 2-[4-(2-thiazolyloxy)phenyl]propionic acid, 2-[3-fluoro-4-(2-thiazolyloxy)phenyl]propionic acid and their metal salts.

In another aspect, the invention provides novel compounds of the formula:

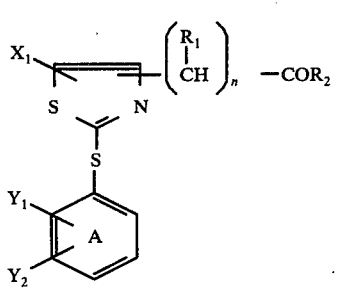

I-3 wherein $R_1$, $R_2$, $n$, $X_1$, $Y_1$ and $Y_2$ each has the same significance designated above.

Illustrative of these compounds represented by formula I-3 and presented as their free acid are the following:
2-phenylthio-5-thiazolecarboxylic acid,
2-(4-methylphenylthio)-5-thiazolecarboxylic acid,
2-phenylthio-5-methyl-4-thiazolecarboxylic acid,
2-phenylthio-4-methyl-5-thiazolecarboxylic acid,
2-(2-phenylthio-4-thiazolyl)acetic acid,
2-(2-phenylthio-4-methyl-5-thiazolyl)acetic acid,
2-[2-(4-methylphenylthio)-4-methyl-5-thiazolyl]acetic acid,
2-(2-phenylthio-5-thiazolyl)propionic acid,
2-(2-phenylthio-4-thiazolyl)propionic acid,
2-(2-phenylthio-4-methyl-5-thiazolyl)propionic acid,
2-[2-(4-chlorophenylthio)-4-methyl-5-thiazolyl]propionic acid,
2-(2-phenylthio-4-thiazolyl)butyric acid,
2-(2-phenylthio-4-thiazolyl)-3-phenylpropionic acid, and the like.

Preferred are the compounds of formula I-3 wherein $X_1$ is hydrogen or methyl, both $Y_1$ and $Y_2$ are hydrogen and $R_1$ is hydrogen or methyl.

The more preferred compound of formula I-3 is 2-(2-phenylthio-4-methyl-5-thiazolyl)acetic acid.

In a further aspect, the invention provides novel compounds of the formula:

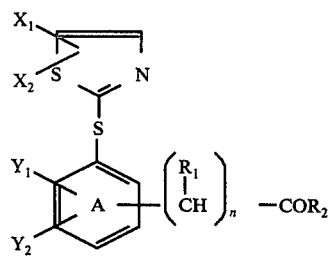

I-4 wherein $R_1$, $R_2$, $n$, $X_1$, $X_2$, $Y_1$ and $Y_2$ each has the same significance designated above and the group

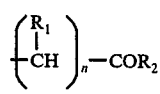

is linked to one of the meta or para positions of the benzene ring A.

Illustrative of these compounds represented by formula I-4 and presented as their free acid are the following:
4-(2-thiazolylthio)benzoic acid,
2-[4-(2-thiazolylthio)phenyl]acetic acid,
2-[3-(2-thiazolylthio)phenyl]propionic acid,
2-[4-(2-thiazolylthio)phenyl]propionic acid,
2-[3-methyl-4-(2-thiazolylthio)phenyl]propionic acid,
2-[4-(2-thiazolylthio)phenyl]-3-cyclopropionic acid,
2-[4-(2-thiazolylthio)phenyl]-3-phenylpropionic acid, and the like.

The compounds of formula I-4 wherein $X_1$ and $X_2$ are independetly is hydrogen or methyl, both $Y_1$ and $Y_2$ are hydrogen and $R_1$ is hydrogen or methyl are preferable.

The more preferred compound is 2-[4-(2-thiazolylthio)phenyl]propionic acid.

In a further aspect, the invention provides novel compounds of the formula:

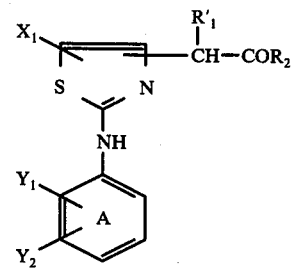

I-5 wherein $R_1'$ is $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl and $R_2$, $X_1$, $Y_1$, and $Y_2$ each has the same significance designated above.

Illustrative of these compounds represented by formula I-5 and presented as their free acid are the following:
2-(2-anilino-5-thiazolyl)propionic acid,
2-(2-anilino-4-thiazolyl)propionic acid,
2-(2-anilino-4-methyl-5-thiazolyl)propionic acid,
2-[2-(3-trifluoromethylanilino)-4-methyl-5-thiazolyl]propionic acid,
2-[2-(3,5-dichloroanilino)-4-thiazolyl]propionic acid,
2-(2-anilino-4-methyl-5-thiazolyl)-3-cyclopropylpropionic acid,
2-(2-anilino-5-ethyl-4-thiazolyl)-3-phenylpropionic acid, and the like.

Preferred are the compounds of formula I-5 of which $X_1$ is hydrogen or methyl, both $Y_1$ and $Y_2$ are hydrogen, $R_1'$ is methyl and $R_2$ is hydroxy.

As the preferred compound, 2-(2-anilino-4-methyl-5-thiazolyl)propionic acid is exemplified.

In other aspect, the present invention provides novel compounds of the formula:

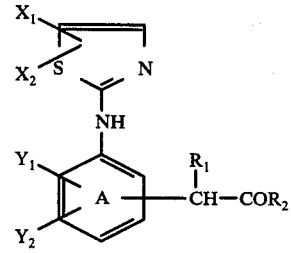

I-6 wherein $R_1$, $R_2$, $X_1$, $X_2$, $Y_1$ and $Y_2$ each has the same significance designated above and the group

is linked to one of the meta or para positions of the benzene ring A.

Illustrative of these compounds represented by formula I-6 and presented as their free acid are the following:
2-[4-(N-thiazol-2-ylamino)phenyl]acetic acid,
2-[3-methyl-5-(N-thiazol-2-ylamino)phenyl]acetic acid,
2-[3-(N-thiazol-2-ylamino)phenyl]propionic acid,
2-[2-chloro-4-(N-thiazol-2-ylamino)phenyl]propionic acid,
2-[3-chloro-4-(N-thiazol-2-ylamino)phenyl]propionic acid,
2-[2-fluoro-4-(N-thiazol-2-ylamino)phenyl]propionic acid, 2-[3-fluoro-4-(N-thiazol-2-ylamino)phenyl]propionic acid,
2-[2-methyl-4-(N-thiazol-2-ylamino)phenyl]propionic acid,
2-[3-(N-thiazol-2-ylamino)-4-methoxyphenyl]propionic acid,
2-[4-chloro-3-(N-thiazol-2-ylamino)phenyl]propionic acid,
2-[3,5-dichloro-4-(N-thiazol-2-ylamino)phenyl]propionic acid,
2-{2-chloro-4-[N-(4-methylthiazol-2-yl)amino]phenyl}propionic acid,
2-{3-fluoro-4-[N-(4-methylthiazol-2-yl)amino]phenyl}propionic acid,
2-{3-methyl-4-[N-(4-methylthiazol-2-yl)amino]phenyl}propionic acid,
2-{3-[N-(4-methylthiazol-2-yl)amino]-4-methylphenyl}propionic acid,
2-{2-fluoro-4-[N-(4-methylthiazol-2-yl)amino]phenyl}propionic acid,
2-[4-(N-thiazol-2-ylamino)phenyl]butyric acid, and the like.

The preferred compounds of formula I-6 are 2-[(N-thiazol-2-ylamino)phenyl]propionic acids which may have one or two substituents selected from methyl, chlorine and fluorine on the benzene ring and methyl on the thiazole ring and the corresponding acetic acid. The group

is preferably linked to the para position of the benzene ring A. They are, for example, 2-[3-chloro-4-(N-thiazol-2-ylamino)phenyl]propionic acid, 2-{3-fluoro-4-(N-(4-methylthiazol-2-yl)amino]phenyl}propionic acid, 2-[3,5-dichloro-4-(N-thiazol-2-ylamino)phenyl]propionic acid, 2-[3-fluoro-4-(N-thiazol-2-ylamino)phenyl]propionic acid and 2-[2-methyl-4-(N-thiazol-2-ylamino)phenyl]propionic acid.

In a further aspect, the invention provides novel compounds of the formula:

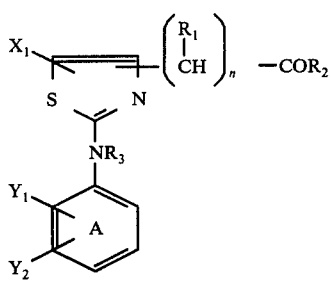

wherein $R_1$, $R_2$, $R_3$, $n$, $X_1$, $Y_1$ and $Y_2$ each has the same significance designated above.

Illustrative of these compounds represented by formula I-7 and presented as their free acid are the following:
2-(N-methylanilino)-4-thiazolecarboxylic acid,
2-(N-methylanilino)-4-methyl-5-thiazolecarboxylic acid,
2-[2-(N-methylanilino)-4-thiazolyl]acetic acid,
2-[2-(N-methylanilino)-5-thiazolyl]acetic acid,
2-[2-(N-methyl-4-chloroanilino)-5-thiazolyl]acetic acid,
2-[2-(N-ethylanilino)-4-thiazolyl]acetic acid,
2-[2-(N-methylanilino)-4-methyl-5-thiazolyl]acetic acid,
2-[2-(N-allylanilino)-4-thiazolyl]acetic acid,
2-[2-(N-allylanilino)-5-thiazolyl]acetic acid,
2-[2-(N-allylanilino)-4-methyl-5-thiazolyl]acetic acid,
2-[2-(N-allyl-4-methylanilino)-5-methyl-4-thiazolyl]acetic acid,
2-[2-(N-cyclopropylmethylanilino)-4-thiazolyl]acetic acid,
2-[2-(N-benzylanilino)-4-thiazolyl]acetic acid,
2-[2-(N-methylanilino)-4-thiazolyl]propionic acid,
2-[2-(N-methylanilino)-5-thiazolyl]propionic acid,
2-[2-(N-ethylanilino)-5-thiazolyl]propionic acid,
2-[2-(N-methylanilino)-4-methyl-5-thiazolyl]propionic acid,
2-[2-(N-methyl-4-methylanilino)-4-methyl-5-thiazolyl]propionic acid,
2-[2-(N-methylanilino)-5-thiazolyl]-3-cyclopropylmetylpropionic acid,
2-[2-(N-cyclopropylmethylanilino)-4-methyl-5-thiazolyl]propionic acid,
2-[2-(N-allylanilino)-4-thiazolyl]propionic acid,
2-[2-(N-allylanilino)-5-thiazolyl]propionic acid,
2-[2-(N-allylanilino)-4-methyl-5-thiazolyl]propionic acid,
2-[2-(N-allylanilino)-4-methyl]butyric acid,
2-[2-(N-benzyl-4-chloroanilino)-5-thiazolyl]propionic acid, and the like.

The compounds of formula I-7 of which $X_1$ is hydrogen or methyl, both $Y_1$ and $Y_2$ are hydrogen, $R_1$ is hydrogen or methyl, $R_2$ is hydroxy, and $R_3$ is methyl and $n$ is 1 are preferred.

The more preferred compounds of formula I-7 are 2-[2-(N-methylanilino)-4-thiazolyl]propionic acid and its metal salt.

In another aspect, the invention provides novel compounds of the formula:

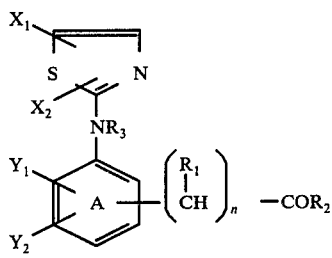

wherein $R_1$, $R_2$, $R_3$, $n$, $X_1$, $X_2$, $Y_1$ and $Y_2$ each has the same significance designated above, and

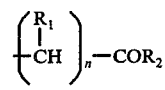

is linked to one of the meta or para positions of the benzene ring A.

Illustrative of these compounds represented by formula I-8 and presented as their free acid are the following:
4-(N-methyl-N-thiazol-2-ylamino)benzoic acid,
2-(3-(N-methyl-N-thiazol-2-ylamino)phenyl]acetic acid,
2-[4-(N-methyl-N-thiazol-2-ylamino)phenyl]acetic acid,
2-[4-(N-allyl-N-thiazol-2-ylamino)phenyl]acetic acid,
2-[2-chloro-4-(N-methyl-N-thiazol-2-ylamino)phenyl]acetic acid, 2-[3-(N-methyl-N-thiazol-2-ylamino)phenyl]propionic acid,
2-[4-(N-methyl-N-thiazol-2-ylamino)phenyl]propionic The objective thiazole derivative I can be prepared by condensation of halogenothiazole with phenyl compounds as follows:

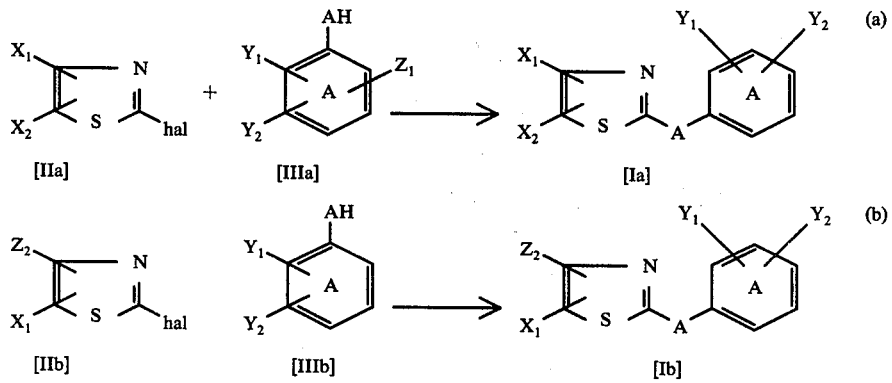

acid,
2-[3,5-dichloro-4-(N-methyl-N-thiazole-2-ylamino)-phenyl]propionic acid,
2-[2-fluoro-4-(N-methyl-N-thiazol-2-ylamino)phenyl]-propionic acid,
2-{3,5-dichloro-4-[N-methyl-N-(4-methylthiazol-2-yl)amino]phenyl}propionic acid,
2-[2-methyl-4-(N-methyl-N-thiazol-2-ylamino)phenyl]-propionic acid,
2-[3-fluoro-4-(N-methyl-N-thiazol-2-ylamino)phenyl]-propionic acid,
2-[4-(N-methyl-N-thiazol-2-ylamino)phenyl]butyric acid,
2-[3-(N-allyl-N-thiazol-2-ylamino)phenyl]propionic acid,
2-[4-(N-allyl-N-thiazol-2-ylamino)phenyl]propionic acid,
2-[4-(N-allyl-N-thiazol-2-ylamino)phenyl]-3-phenylpropionic acid,
2-[4-(N-cyclopropylmethyl-N-thiazol-2-ylamino)-phenyl]propionic acid,
2-[4-(N-benzyl-N-thiazol-2-ylamino)phenyl]propionic acid, and the like.

Among the preferred compounds of formula I-8 are 2-[(N-methyl-N-thiazol-2-ylamino)phenyl]propionic acids which may have one or two substituents selected from methyl, flourine or chlorine on the benzene ring and methyl on the thiazole ring and the corresponding acetic acid. The group

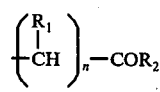

preferably substituents the para position. They are, for example, 2-[2-methyl-4-(N-methyl-N-thiazole-2-ylamino)phenyl]propionic acid, 2-[3-fluoro-4-(N-methyl-N-thiazole-2-ylamino)phenyl]propionic acid, 2-[3,5-dichloro-4-(N-methyl-N-thiazol-2-ylamino)-phenyl]propionic acid, 2-{3,5-dichloro-4-[N-methyl-4-(4-methylthiazol-2-yl)amino]phenyl}propionic acid,
2-[4-(N-methyl-N-thiazol-2-ylamino)phenyl]acetic acid and
2-[4-(N-methyl-N-thiazol-2-ylamino)phenyl]propionic acid.

The compounds of the present invention can be prepared by various methods. One of the preferred methods is condensation.

wherein A, $X_1$, $X_2$, $Y_1$ and $Y_2$ each has the same significance designated above; hal is chlorine, bromine or iodine; and $Z_1$ and $Z_2$ each is a group which can be converted to —COOH or

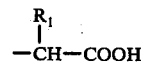

by hydrolysis wherein $R_1$ has the same significance designated above but $Z_1$ is linked to one of the meta or para positions of the benzene ring A and is not a group converted to —COOH when A is imino and $Z_2$ is not a group converted to —COOH and $CH_2COOH$ when A is imino.

The objective compound I can be prepared by condensation of 2-halogenothiazole derivative with a phenyl compound followed by hydrolysis, if necessary. More precisely, condensation of 2-halogenothiazole derivative IIa with phenyl compound IIIa in accordance with scheme (a) optionally followed by hydrolysis of the resultant compound Ia gives the compound I having the group

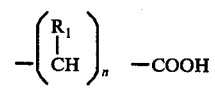

($n$ is an integer of 0 or 1) at the benzene ring A. The same procedure with thiazole derivative IIb and phenyl compound IIIb provides the compound 1 substituted at the thiazole ring by the group

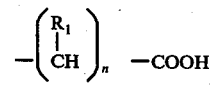

The substituents $Z_1$ and $Z_2$ are exemplified by the corresponding nitrile, amide or esters.

Both reactions represented by scheme (a) and (b) can be executed in the same condition. The compound IIa or IIb is condensed with the compound IIIa or IIIb in the presence of base. Generally, the reaction may be executed at a temperature ranging from about 20° C to about 200° C, namely from at room temperature to the boiling point of the solvent, if employed, in the presence of base.

The bases to be used are, for example, alkali metal hydroxides (e.g. sodium hydroxide, potassium hydroxide), alkali metal carbonates (e.g. sodium carbonate, potassium carbonate), alkali metal hydrogen carbonates (e.g. sodium hydrogen carbonate, potassium hydrogen carbonate), alkali metal acetates (e.g. sodium acetate, potassium acetate).

Metal catalyst (e.g. copper powder, cupric oxide) can be employed to acceralate the reaction, when phenol derivatives are used as starting compound IIIa or IIIb. Further, the reaction may be practised without base if a basic starting material such as aniline derivative is used. The reaction solvent is not necessarily required, but may be selected from inert solvents, for example, aromatic hydrocarbons (e.g. benzene, toluene, xylene, pyridine), aliphatic hydrocarbons (e.g. pentane, hexane, heptane), alcohols (e.g. methanol, ethanol, propanol), dimethylacetoamide and the like. They can be employed solely or as a mixture in consideration of the solubility of the saarting compounds as well as other reaction conditions employed. The reaction may be effected without other solvent by use of an excess of liquid starting compound.

The product may be subjected to hydrolysis, if necessary. The hydrolysis can be executed by the usual method used to hydrolyze nitriles, amides or esters to the corresponding carboxylic acid. Namely, the product is hydrolyzed with acids (e.g. hydrochloric acid, sulfuric acid, hydrobromic acid, acetic acid) or bases (e.g. sodium hydroxide, potassium hydroxide, sodium carbonate, potassium carbonate, sodium hydrogen carbonate, potassium hydrogen carbonate) in water or other organic solvent containing water. The reaction can be practised at room temperature or under heating.

The starting compound IIa can be prepared by the method described on pages 539–541 and 545–547 of "Heterocyclic Compound, Vol. 5" by Elderfield.

Another starting compound IIIa of which $Z_1$ is nitrile, amide or carboxylic acid ester is commercially available. Other compound IIIa of which $Z_1$ is a group convertible to

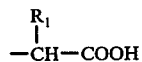
—CH—COOH can be prepared by several methods. A method starting with p- or m-hydroxy (or m- and p- mercapto-) benzoic acid gives compound IIIa of which A is oxygen (or sulfur). Illustrative of p-hydroxyphenylacetic acid and α-substituted-α-(p-hydroxyphenyl)acetic acid is as follows:

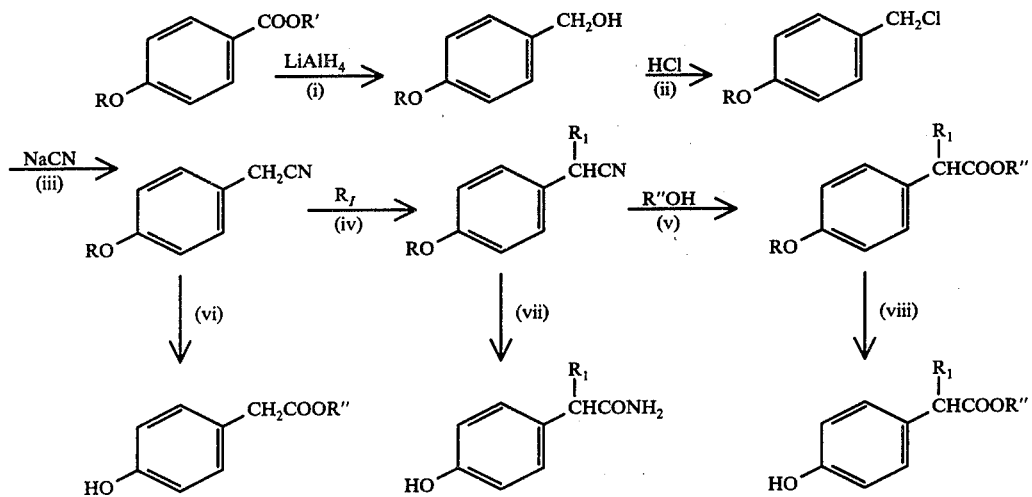

wherein R is hydroxy group-protecting group, R' and R" each represents ester residue and $R_1$ has the same significance designated above.

Step $i$ is hydrogenation of benzoic acid and step $ii$ consists of halogenation of benzylalcohol. The next step $iii$ is cyanation and may be executed in a usual manner with cyanating agent (e.g. sodium cyanide, potassium cyanide, cuprous cyanide) in an inert solvent (e.g. pyridine, dimethylformamide, ethanol) under heating. Step $iv$ consists of condensation of p-hydroxyphenylacetonitrile with halogenohydrocarbon. The halogenohydrocarbon to be used is iodide, bromide or chloride of alkane (e.g. methane, ethane, propane, i-propane, butane, pentane, i-pentane), alkene (e.g. ethene, propene, butene, i-butene, pentene) and alkynes (e.g. propyne, butyne-1, pentyne-2), cycloalkylalkane (e.g. cyclopropylmethane, cyclopropylethane, cyclobutylmethane, cyclopentylethane, cyclohexylmethane), arylalkane (e.g. toluene, ethylbenzene). The reaction may be effected in the presence or absence of condensing agent such as alkali metal, alkali metal alkoxide, butyl lithium and sodium hydroxide.

Step $v$ is alcoholysis of nitrile group which can be effected in a suitable aliphatic or aromatic alcohol.

Step $vi$ and step $vii$ are hydrolysis which can be executed in a conventional manner with acids (e.g. hydrochloric acid, sulfuric acid) or bases (e.g. sodium hydroxide, potassium hydroxide) in water or inert organic solvent containing water.

Step $viii$ is removal of protecting group of hydroxy group and can be effected by a conventional procedure.

m-Hydroxy compound can be prepared in the same manner. Thiol compound of IIIa can be obtained by using p- or m-mercapto benzoic acid and its equivalent. The thiol compound can be also prepared by diazotation of the corresponding aniline derivative of formula IIIa followed by condensation with potassium xanthogenate and hydrolysis of the resultant compound. A starting compound IIIa having one or two substituents can be prepared by following the above process with substituted benzoic acid and its equivalent. For example, ethyl 2-(2-methyl-4-hydroxyphenyl)propionate can be prepared from ethyl 2-methyl-4-benzyloxy benzoate.

A starting compound IIIa of which A is NR₃ can be prepared by the following process:

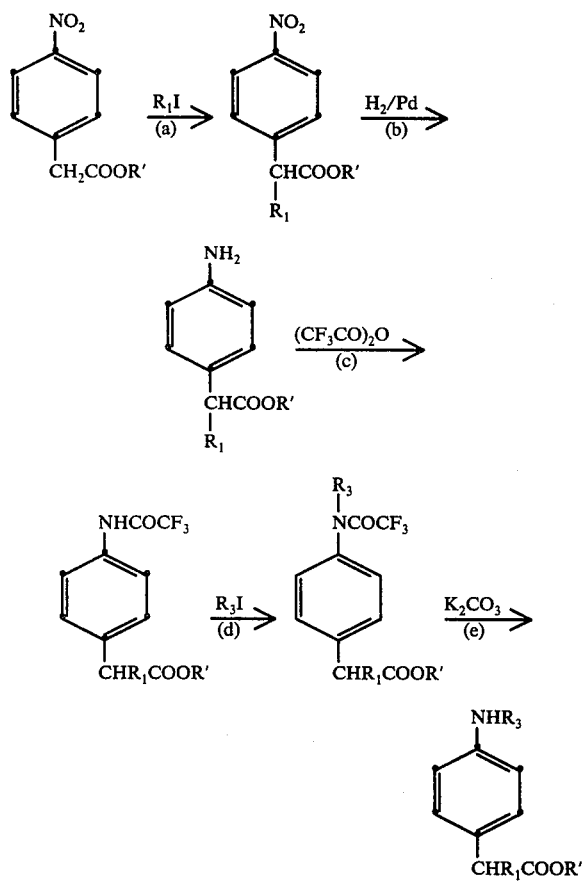

wherein R' is ester residue and R₁ and R₃ each has the same significance designated above.

Step *a* and *d* are effected in the same manner as in step iv for preparing compound IIIa described above. Step *b* is reduction usually with palladium. Step *c* is smoothly effected with trifluoroacetic anhydride under cooling. Step *e* is basic hydrolysis in a usual manner.

m-Amino and m-imino compounds IIIa can be prepared in the same manner by starting with m- or p-nitrophenylacetate.

Thiazole derivative IIb can be prepared according to any of a variety of methods. Ester of 2-amino-4- and 5-thiazolecarboxylic acids can be prepared by any method described in "Heterocyclic Compound", Elderfield, 5, 624. For example, reaction of bromopyruvic acid with thiourea gives 2-amino-4-thiazolecarboxylic acid (J. Am. Chem. Soc. 68, 266 (1946)) which is subjected to the Gattermann reaction to give 2-halogeno derivatives. Ester of 2-halogeno-5-methyl-4-thiazolecarboxylic acid can be obtained from 2-chloro-2,3-epoxybutyric acid ester with thiourea (Bull. Chem. Soc. Jap. 43, 2997 (1970)). Ethyl 2-halogeno-4-methyl-5-thiazolecarboxylate can be prepared from ethyl α-chloroacetoacetate with thiourea (J. Pharm. Soc. Jap., 76, 301 (1956)). These compounds are subjected to the Arndt-Eistert reaction with diazomethane or diazoethane or alkylation to give the corresponding acetic or propionic acid. Further, ethyl 2-chloro-4-methyl-5-thiazolecarboxylate can be prepared from ethyl 3-thiocyano-3-acetoxypropionate according to the method shown in U.S. Pat. No. 2,319,570. Ethyl 2-(2-bromo-4-thiazolyl)propionate is also prepared from ethyl 2-bromoacetylpropionate with thiourea (J. Am. Chem. Soc. 63, 2946 (1941)). Thiazole derivative IIb substituted with an alkyl group other than methyl can be prepared by condensation following the method described above or alkylation of the thiazole derivatives prepared above.

The starting compound IIIb is phenol, thiophenol, aniline, or the mono- or di-substituted derivative. They are commercially available or can be prepared by the conventional method. Another compound IIIb, N-substituted aniline is prepared according to the process as follows:

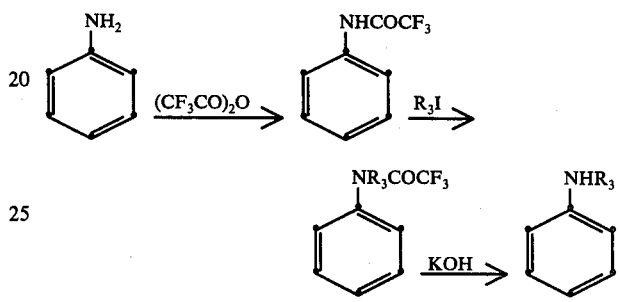

wherein R₃ has the same significance designated above. The first step is the same as the step *c* for preparing compound IIIa and the second is as step *d*. For Example, N-allylaniline is prepared N-trifluoroacetylaniline with allylbromide. N-cyclopropylmethylaniline can be obtained in the same manner and also prepared by reduction of N-cyclopropylcarbonylaniline.

Thus prepared compound I having thiazolecarboxylic acid or benzoic acid residue can be used to prepare other compound I by elongating the carboxyl group to a desired acid residue.

Thus, prepared compound of fromula I, more specifically I-1, I-2, I-3, I-4, I-5, I-6, I-7 and I-8 can be converted to the salts in conventional manner in accordance with requirement for separation, purification, formulation and so on. The above product is treated with base to give alkali metal salts (e.g. sodium salt, potassium salt, lithium salt), alkaline earth metal salts (e.g. calcium salt, aluminium salt). The calcium salt is preferred.

Besides, some of compounds I are an optically active compound and may be resolved into d-isomer and l-isomer. The optical resolution can be executed in a conventional manner and both isomers can be used solely or as a mixture depending on the therapeutical requirement.

Thus obtained compounds I including the non-toxic salts are useful as medicament having anti-inflammatory, anti-rheumatic, analgesic and anti-lipemia activities.

The following table indicates the activities of representative compounds of the present invention, i.e. calcium 2-(2-phenoxy-4-methyl-5-thiazolyl)propionate (signified by 48-140 in the table) and 2-[4-(2-thiazolyloxy)phenyl]propionic acid (signified by 48-156 in the table), in comparison with those of commercially available anti-inflammatory and analgesic agents, acetylsalicylic acid and phenylbutazone.

| Assay Item | Drug mg/kg ED (%) | Acetyl-Salicylic Acid | Phenyl-butazone | 48-140 | 48-156 |
|---|---|---|---|---|---|
| 1. Anti-edema | 30 | 48 | 48 | 14 | 3.8 |
| 2. Anti-abscess | 25 | 175 | 33 | 60 | 6.4 |
| 3. Anti-granuloma | 25 | >500 | 24 | 230 | 13 |
| 4. Anti-erythema | 50 | 79 | 26 | 27 | 20 |
| 5. Arthritis | 30 | 100 | 7.8 | 20 | 4.2 |
| 6. Acetic Acid Writhing | 50 | 180 | 440 | 180 | 20 |
| 7. Scald-inflamed Foot | 100 | 260 | 240 | >500 | 77 |
| 8. Yeast-inflamed Foot | 100 | 250 | 130 | 110 | 28 |
| 9. Footlicking | 50 | 580 | 150 | 130 | 175 |
| 10. Adjuvant Arthritic Pain* | | 200 | 7 | 25 | 3.4 |
| 11. Anti-pyretic Activity** | | 14 | 3.8 | 23 | 4 |
| 12. Acute Toxicity Mouse | | 1998 | 1414 | 1190 | 1799 |
| Rat | | 2401 | 874 | 1200 | 154 |

Note: *Figures represent the dose by which animals bear the pain caused by the pressure of 175 g.
**Figures represent the dose by which body temperature is reduced 0.5° C.

Test Method

1. Anti-edema Activity

An aqueous solution of 1% carrageenin (0.05 ml) is used as phlogistic agent. After 30 minutes Wistar rats (180–200 g, female) are orally administered test compounds, the phalogistic agent is injected subcutaneously into the plantar parts of the foot of rats. The volume of swelling is measured 3 hours after carrageenin, and the anti-edema activity is determined by calculating the ratio of the edematous volume of medicated foot to that of non-medicated foot. The $ED_{50}$ is calculated by the Bliss' method.

2. Anti-abscess Activity

Carrageenin (2% aqueous solution, 0.5 ml) is subcutaneously injected into the back of Wistar rats (180–200 g, female) and at the same time one-half dose of a test compound is orally given, the other half given 3 hours later. The animals are sacrificed 24 hours after carrageenin and the abscess formed is isolated and weighed. The $ED_{25}$ is calculated by the Bliss' method.

3. Anti-granuloma Activity

Two circular pieces of filterpaper about 6 mm in diameter, soaking 90 mg of 5% carrageenin solution, are implanted subcutaneously in the abdominal skin of Wistar rat (180–200 g, female). A test drug is orally given once a day for 6 consecutive days. On the 7th day the animals are killed and the amount of granulation tissue deposited, the adrenals and the thymus are weighed. The $ED_{25}$ is calculated by the Bliss' method.

4. Anti-erythema Activity

The hair on the back of guinea-pig (300–400 g, male and female) is removed on the day before experiment. Thirty minutes after oral administration of a test drug, 3 circular areas (8 mm in diameter each) on the back of the animal are exposed to ultraviolet light for 60 seconds. Anti-erythema activity is evaluated at 2 hours after irradiation. The $ED_{50}$ is calculated by Up and Down method of Brownlee et al. [J. Am. Stat. Assoc. 48, 262 (1953)].

5. Effect on Adjuvant Arthritis

Wistar rat (140–160 g. female) exhibiting a typical arthritis in the foot by the 21st day after intradermal injection of dead tubercle bacilli is selected for the test. A test compound is orally administered to the arthritic rat twice a day for 5 consecutive days. Five hours after the final medication the change in swelling volume of the arthritic foot is measured. The $ED_{30}$ is calculated by the Bliss' method.

6. Acetic Acid Writhing Method

DS mice (20–23 g, male) are treated with an intraperitoneal injection of 0.1 ml/10 g of 0.6% acetic acid 60 minutes after oral administration of a test drug. The number of times of writhing for 10 minutes is counted. The $ED_{50}$ is calculated by the Bliss' method.

7. Effect on Scald-inflamed Foot

The inflammation is produced by immersing one leg of Wistar rat (180–200 g, female) in hot water (58.5° C) for 5 seconds. A test drug is administered orally 90 minutes after scalding and the analgesic activity is evaluated by compressing the foot with a plunger. The pain threshold is calculated by the method of Litchfield and Wilcoxon [J. Pharmacol. Exp. Ther. 96, 99–113 (1949)].

8. Effect on Yeast-inflamed Foot

A test compound is orally given Wistar rat (180–200 g, female) immediately before subcutaneous injection of 0.1 ml of 20% yeast suspension into the plantar tissue of the foot. Two hours later, the pain threshold is measured by comprissing the foot with a plunger and calculated by the method of Litchfield and Wilcoxon.

9. Foot-licking Method

Thirty minutes after oral administration of a test drug in Wistar rat (180–200 g, female), the effect of the compound on foot-licking syndrome due to irritation by a subcutaneous injection of 0.05 ml of 3.75% formaldehyde into the planter tissue of the hind-paw is observed for 50 minutes. The $ED_{50}$ is calculated by the method of Litchfield and Wilcoxon.

10. Effect on Adjuvant Arthritic Pain

Wistar rat (140–160 g, female) exhibiting a typical arthritis in the foot by the 21st day after intradermal injection of dead tubercle bacilli is selected for the test. After oral administration of a test drug, the pain threshold of the arthritic foot is determined every 1 hour by comprissing the ankle joint with intestinal forceps and calculated by the method of Litchfield and Wilcoxon.

11. Anti-pyretic Activity

A test compound is orally administered to Wister rat (180–200 g, female) 16 hours after an injection of 2 ml of 15% suspension of yeast into the subcutaneous tissue of the hip of the rat. The rectal temperature is measured every 1 hour for 5 hours. The effective dose is calculated by the Bliss' method.

12. Acute Toxicity

Ten DS mice (20–23 g, male) or ten Wister rats (180–200 g, female) a group are used at one dose level. The $LD_{50}$ after 72 hours of oral administration of a test drug is determined. The $LD_{50}$ is calculated by the Bliss' method.

As indicated above, the thiazole derivatives show more potent anti-inflammatory, anti-rheumatic and analgesic activities than the commercially available analgesic and anti-inflammatory agents, acetylsalicylic acid and phenylbutazone.

Compounds I, more precisely compounds I-1, I-2, I-3, I-4, I-5, I-6, I-7 and I-8, and their non-toxic salts show anti-inflammatory, anti-rheumatic and analgesic activities and are useful as medicament. They can be used in treatment of various rheumatic diseases, inflammation, pains and lipemia solely or in combination with a pharmaceutically acceptable carrier. The carrier to be used is determined by the solubility and chemical property of the compound, and the route of administration. There are exemplified as solid carrier for internal or external use lactose, sucrose, starch, dextrin, sodium hydrogen carbonate, licorice powder, talc, kaolin, bentonite, calcium carbonate, paraffin and as gel or liquid carrier gelatine, water, ethanol, i-propanol, chloroform, glycerol and the like. Freon (Trade Mark) is also available for aerosols.

Practical examples of suitable pharmaceutical preparations of compound I are tablets, capsules, pills, ointment, granules, powders, suppositories, aerosols or injectable solutions.

Therapeutic composition comprises 1 mg to 100 mg of one or more compounds of general formula I, more precisely formulas I-1, I-2, I-3, I-4, I-5, I-6, I-7 and I-8 with or without a pharmaceutically acceptable carrier. The compound I generally administered to man and animals in the order of the same to one tenth of the practical dosage of phenylbutazone, i.e. 20–400 mg of compound I i.e. I-1, I-2, I-3, I-4, I-5, I-6, I-7 and I-8 can be administered to man orally either in single or divided doses over a period of 24 hours.

The following examples are given solely for the purpose of illustration and not to be construed as limitation of the present invention.

EXAMPLE 1

A mixture of 2-chlorothiazole (5.0 g), ethyl 2-(4-hydroxyphenyl)propionate (8.1 g), potassium carbonate powder (8.65 g) and dimethylformamide (80 ml) is stirred at 150°–155° C for 2.5 hours. The solvent is distilled out under reduced pressure. To the residue is added water and extracted with ether. The extract is washed with a 10% aqueous solution of sodium hydroxide and water and dried. The ether is evaporated. The residue is subjected to chromatography using silica gel and eluted with 50% benzene-hexane, benzene and 10% ether-benzene to yield ethyl 2-[4-(2-thiazolyloxy)phenyl]propionate (5.8 g.). IR $\nu_{max}^{CCl_4}$ 1740, 1240, 700 cm$^{-1}$.

The product is dissolved in a mixture of a 20% aqueous solution of potassium hydroxide (30 ml) and 95% ethanol (30 ml). The solution is kept at room temperature for 30 minutes. The solvent is evaporated. The residue is acidified with hydrochloric acid after addition of water, and extracted with ether. The extract is washed with water and dried over magnesium sulfate. The solvent is distilled out. The residue is recrystallized from ether-hexane to give 2-[4-(2-thiazolyloxy)phenyl]propionic acid (4.8 g). IR $\nu_{max}^{Nujol}$ 2520, 1715 cm$^{-1}$. Anal. Calcd. for $C_{12}H_{11}O_3NS$: C, 57.81; H, 4.45; N, 5.62; S, 12.86 Found: C, 57.72; H, 4.50; N, 5.69; S, 12.70.

The product (5.0 g) is dissolved in an aqueous solution (30 ml) of sodium hydroxide (0.82 g). To the solution washed with ether is added an aqueous solution (5 ml) of calcium chloride 2 hydrate (1.6 g) to form a precipitate. The precipitate washed with water gives calcium 2-[4-(2-thiazolyloxy)phenyl]propionate (5.5 g) melting at 143°–145° C. IR $\nu_{max}^{Nujol}$ 3400, 1570 cm$^{-1}$. Anal. Calcd. for $(C_{12}H_{10}O_3NS)_2 \cdot 2H_2O$: C, 50.33; H, 4.22; N, 4.89; Ca, 7.00 Found: C, 50.07; H, 4.37; N, 4.91; Ca, 7.18.

EXAMPLE 2

A mixture of 2-chlorothiazole (2.0 g), ethyl 4-hydroxybenzoate (2.8 g), potassium carbonate powder (3.5 g) and dimethylformamide (30 ml) is stirred at 135°–140° C for 6 hours. The reaction mixture is treated in the same manner as in Example 1. From the eluate of 30% ether-benzene, ethyl 4-(2-thiazolyloxy)benzoate (1.16 g) is obtained. IR $\nu_{max}^{CCl_4}$ 1730, 1280 cm$^{-1}$.

The product is hydrolyzed in the same manner as in Example 1 and recrystallized from ethanol to give 4-(2-thiazolyloxy)benzoic acid (1.00 g) melting at 162°–163° C. IR $\nu_{max}^{Nujol}$ 1680, 1240 cm$^{-1}$. Anal. Calcd. for $C_{12}H_{11}O_3NS$: C, 54.29; H, 3.19; N, 6.33; S, 14.49. Found: C, 54.48; H, 3.13; N, 6.34; S, 14.24.

Treatment in the same manner gives 2-chloro-3-methyl-4-(2-thiazolyloxy)benzoic acid melting at 150°–152° C.

EXAMPLE 3

A suspension of 2-bromothiazole (8.3 g), ethyl 3-fluoro-4-hydroxybenzoate (7.6 g), potassium carbonate powder (8.7 g) and cupric oxide (1 g) in pyridine (100 ml) is stirred at 160° C for 24 hours. The reaction mixture is filtered and the precipitate is washed with benzene. The filtrate and washings are combined. The solvent is distilled out. The residue is dissolved in benzene. The solution is washed with a 10% aqueous solution of sodium hydroxide and water successively, dried and the solvent is evaporated. The residue is subjected to chromatography using silica gel. From benzene and 2% ether-benzene eluates ethyl 3-fluoro-4-(2-thiazolyloxy)benzoate (2.2 g) is obtained.

The product is subjected to hydrolysis in the same manner as in Example 1 and recrystallized from ether gives 3-fluoro-4-(2-thiazolyloxy)benzoic acid melting at 133°–134° C. Anal. Calcd. for $C_{12}H_6O_3NSF$: C, 50.21; H, 2.53; N, 5.86; S, 13.40; F, 7.94 Found: C, 50.44; N, 2.66; N, 5.71; S, 13.73; F, 7.62.

EXAMPLE 4

Ethyl 2-bromo-5-thiazolecarboxylate (10 g), phenol (4.38 g) and potassium carbonate powder (11.7 g) are suspended in dimethylformamide (50 ml) and the suspension is stirred for 3 hours at 80° C. The reaction mixture is treated in the same manner as in Example 1 to give ethyl 2-phenoxy-5-thiazolecarboxylate (10.2 g) boiling at 127°–128° C at 1 mmHg.

The product is subjected to hydrolysis in the same manner as in Example 1 and recrystallized from acetone to give 2-phenoxy-5-thiazolecarboxylic acid (8.56 g) melting at 172°–173° C. IR $\nu_{max}^{Nujol}$ 2400, 1840, 1710 cm$^{-1}$. Anal. Calcd. for $C_{10}H_7O_3NS$: C, 54.29; H, 3.19; N, 6.33; S, 14.49 Found: C, 54.32; H, 3.12; N, 6.25; S, 14.48.

EXAMPLE 5

Treatment in the same manner as in Example 1 gives 2-(2-phenoxy-4-methyl-5-thiazolyl)propionic acid. Recrystallization from ether-hexane gives crystals melting at 109°–110° C.

EXAMPLE 6

A suspension of ethyl 2-bromo-4-methyl-5-thiazolecarboxylate (22 g), thiophenol (10.75 g) and potassium carbonate powder (24.3 g) in dimethylformamide (100 ml) is stirred for 4 hours at 80° C. The reaction mixture is treated in the same manner as in Example 1 to give ethyl 2-phenylthio-4-methyl-5-thiazolecarboxylate (24.2 g) boiling at 160°–161° C at 1 mmHg.

The product is subjected to hydrolysis in the same manner as in Example 1 and recrystallized from acetone to yield 2-phenylthio-4-methyl-5-thiazolecarboxylic acid (20.8 g) melting at 187°–188° C. IR $\nu_{max}^{Nujol}$ 2570, 2460, 1710 cm$^{-1}$. Anal. Calcd. for $C_{11}H_9O_2NS_2$: C, 52.57; H, 3.61; N, 5.57; S, 25.52 Found: C, 52.51; H, 3.68; N, 5.42; S, 25.53.

EXAMPLE 7

A mixture of 2-bromothiazole (3.9 g) and ethyl 2-(4-mercaptophenyl)propionate (4.56 g), potassium carbonate powder (4.9 g) and dimethylformamide (50 ml) is stirred at 85° C overnight. The reaction mixture is treated in the same manner as in Example 6 to give 2-[4-(2-thiazolylthio)phenyl]-propionic acid melting at 85°–87° C.

EXAMPLE 8

A mixture of methyl 2-(2-chloro-4-methyl-5-thiazolyl)propionate (1.40 g) and aniline (1.18 g) is heated to 180° C and kept for 10 minutes at the same temperature. After cooling, to the mixture is added water and extracted with benzene. The extract is washed with water, dried and evaporated under reduced pressure. The residue is subjected to chromatography using alumina and eluted with benzene. The eluate is evaporated to give oily residue (1.70 g).

The product is subjected to hydrolysis in the same manner as in Example 1 to give 2-(2-anilino-4-methyl-5-thiazolyl)propionic acid (1.0 g). Recrystallization from ethanol gives crystals (670 mg) melting at 145° C (decomp.). IR $\nu_{max}^{Nujol}$ 3460, 3260, 2600, 1630 cm$^{-1}$. Anal. Calcd. for $C_{13}H_{14}O_2N_2S \cdot 1/2C_2H_5OH$: C, 58.92; H, 6.00; N, 9.82; S, 11.24 Found: C, 58.79; N, 5.88; N, 10.04; S, 11.43.

EXAMPLE 9

A mixture of ethyl 2-(3-fluoro-4-aminophenyl)propionate (15 g) and 2-bromothiazole (11.7 g) is stirred at 150°–155° C for 15 minutes. The reaction mixture is dissolved in methylene chloride and the solution is washed with an aqueous solution of sodium hydrogen carbonate and dried. The solvent is evaporated. The residue is subjected to chromatography using alumina. From benzene eluate, ethyl 2-[3-fluoro-4-(N-thiazol-2-ylamino)phenyl]propionate (13.3 g) is obtained as oily substance boiling at 162°–164° C at 0.2 mmHg.

To the product (6.1 g) is added 20% hydrochloric acid (61 ml) and the mixture is refluxed for 1.5 hours. After cooling, the solution is made alkaline, then adjusted to pH 4 with acetic acid and extracted with ether. The extract is washed with water, dried and evaporated to give 2-[3-fluoro-4-(N-thiazol-2-ylamino)phenyl]propionic acid (5.5 g). Recrystallization from ethyl acetate gives crystals melting at 160°–161° C. IR $\nu_{max}^{Nujol}$ 3260, 3140, 3080, 2400, 1900, 1695, 1635, 1605 cm$^{-1}$. Anal. Calcd. for $C_{12}H_{11}O_2N_2SF$: C, 54.12; H, 4.16; N, 10.52; S, 12.04; F, 7.14 Found: C, 54.10; H, 4.43; N, 10.50; S, 12.15; F, 7.34.

EXAMPLE 10

A mixture of ethyl 2-(N-methylaminophenyl)propionate (9.4 g) and 2-bromothiazole (7.5 g) is stirred at 100°–145° C for 25 minutes. The reaction mixture is treated in the same manner as in Example 1 to give ethyl 2-[4-(N-methyl-N-thiazol-2-ylamino)phenyl]propionate (3.89 g).

The product is hydrolyzed in the same manner as in Example 1 and crystallized from ether-hexane (1:1) to give 2-[4-(N-methyl-N-thiazol-2-ylamino)phenyl]propionic acid melting at 121°–123° C. Recrystallization from 95% ethanol gives crystals melting at 123°–124° C. IR $\nu_{max}^{Nujol}$ 2500, 1900, 1710, 1500 cm$^{-1}$. Anal. Calcd. for $C_{13}H_{14}O_2N_2S$: C, 59.52; H, 5.38; N, 10.68; S, 12.22 Found: C, 59.27; H, 5.49; N, 10.42; S, 12.32.

EXAMPLE 11

A mixture of ethyl 2-bromo-4-thiazolylacetate (2.5 g) and N-methylaniline (2.1 g) is stirred at 150°–155° C for 30 minutes. The resultant solution is treated in the same manner as in Example 1 to give ethyl 2-(N-methylanilino)-4-thiazolylacetate (2.5 g).

The product is hydrolyzed in the same manner as in Example 1 and recrystallized from ethyl acetate-hexane to give 2-(N-methylanilino)-4-thiazolylacetic acid (1.5 g) melting at 99°–100° C (decomp.). IR $\nu_{max}^{Nujol}$ 2500, 1970, 1730 cm$^{-1}$. Anal. Calcd. for $C_{12}H_{12}O_2N_2S$: C, 58.06; H, 4.87; N, 11.29; S, 12.89 Found: C, 57.94; H, 4.90; N, 11.17; S, 12.62.

Treatment in the same manner as described above gives 2-[2-(N-allylanilino)-5-thiazolyl]propionic acid (0.2 g) melting at 134°–135° C from ethyl 2-(2-chloro-5-thiazolyl)propionate (1.2 g) and N-allylaniline (1.45 g).

EXAMPLES 12–22

Treatment in the same manner as in Example 4 gives the following compounds:

| Ex. No. | $Y_1$ | $Y_2$ | A | X | R | bp or mp (° C) | mp (° C) R=H |
|---|---|---|---|---|---|---|---|
| 12 | H | H | O | 4-CH$_3$ | C$_2$H$_5$ | bp$_{1.5}$ 154 | 227–228(d) |
| 13 | 2-CH$_3$ | 3-CH$_3$ | O | " | " | mp 65–66 | 178–180 |
| 14 | 3-CH$_3$ | H | O | " | " | bp$_1$ 120 | 145–146 |
| 15 | 4-CH$_3$ | H | O | " | " | bp$_1$ 129 | 211–212 |
| 16 | 4-Cl | H | O | " | " | bp$_1$ 140 | 219–220 |
| 17 | 4-Cl | H | O | 4-H | " | mp 66–67 | 210–211 |
| 18 | H | H | O | " | " | bp$_{0.3}$ 133–135 | 177–178 |
| 19 | 4-Cl | H | O | 5-CH$_3$ | CH$_3$ | mp 82–82.5 | 158–159 |
| 20 | H | H | O | " | C$_2$H$_5$ | bp$_1$ 160 | 92–94 |
| 21 | 4-Cl | H | O | 5-H | " | mp 92–93 | 214–215 |

-continued

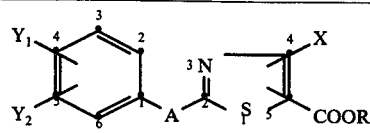

| Ex. No. | $Y_1$ | $Y_2$ | A | X | R | bp or mp (°C) | mp (°C) R=H |
|---|---|---|---|---|---|---|---|
| 22 | H | H | S | " | " | mp 84–85 | 226–227 | d: decomposition

EXAMPLES 23–56

Treatment in the same manner as in Example 1 or 9 gives the following compounds:

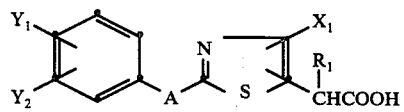

| Ex. No. | $Y_1$ | $Y_2$ | A | $X_1$ | $R_1$ | mp (°C) |
|---|---|---|---|---|---|---|
| 23 | H | H | O | 5-H | H | Ca.½H₂O 120–122 |
| 24 | H | H | O | 4-CH₃ | H | 120–121 |
| 25 | H | H | O | 5-H | CH₃ | Ca.2½H₂O 142(d) |
| 26 | H | H | O | 5-CH₃ | " | Ca.2½H₂O 142(d) |
| 27 | 4-Cl | H | O | 5-H | " | Ca.2½H₂O 133–135 |
| 28 | " | H | O | 5-CH₃ | " | Ca.2½H₂O 134–136(d) |
| 29 | H | H | O | 4-CH₃ | H | Ca.½H₂O 124(d) |
| 30 | H | H | O | 4-H | CH₃ | Ca.1½H₂O 169–170(d) |
| 31 | H | H | O | 4-CH₃ | " | 111.5–112.5 |
| 32 | 4-Cl | H | O | 4-H | " | Ca.H₂O 145(d) |
| 33 | 4-Cl | H | O | 4-CH₃ | " | Ca.2½H₂O 133(d) |
| 34 | 4-CH₃ | H | O | 4-CH₃ | " | Ca.2½H₂O 146(d) |
| 35 | 3-CF₃ | H | O | 4-CH₃ | " | Ca.1½H₂O 106(d) |
| 36 | 2-CH₃ | 3-CH₃ | O | 4-CH₃ | " | 142–143 |
| 37 | H | H | S | 5-H | H | 112–113 |
| 38 | H | H | S | 4-CH₃ | H | 195–196 |
| 39 | H | H | S | 4-CH₃ | CH₃ | 128–130 |
| 40 | H | H | NH | 5-H | H | ½CH₃COCH₃ 140(d) |
| 41 | 3-CF₃ | H | NH | 4-CH₃ | CH₃ | ½CH₃COCH₃ 195(d) |
| 42 | H | H | N—CH₃ | 4-H | H | 186–187 |
| 43 | H | H | N—CH₃ | 4-CH₃ | H | Ca.2H₂O 181(d) |
| 44 | H | H | N—CH₃ | 5-H | CH₃ | Ca.2H₂O 145–147 |
| 45 | H | H | N—CH₃ | 4-H | " | 198–200 |
| 46 | H | H | N—CH₃ | 4-CH₃ | " | 141–142 |
| 47 | H | H | N—CH₂—CH=CH₂ | 5-H | H | Ca.2H₂O 113–115 |
| 48 | H | H | " | 5-H | CH₃ | Ca.2H₂O 173–178(d) |
| 49 | H | H | " | 4-H | H | 119–120 |
| 50 | H | H | " | 4-CH₃ | H | 116–117 |
| 51 | H | H | " | 4-CH₃ | CH₃ | 106–107 |
| 52 | H | H | N—CH₂—C₃H₅ | 5-H | H | Ca.2H₂O 133–136(d) |
| 53 | H | H | " | 5-H | CH₃ | Ca.3H₂O 180–183 |
| 54 | H | H | " | 4-CH₃ | " | 120–121 |
| 55 | H | H | N—CH₂—C₆H₅ | 5-H | H | Ca.½H₂O 140–145(d) |
| 56 | H | H | " | 5-H | CH₃ | Ca.H₂O 120–125(d) |

Ca: Calcium salt
H₂O: Hydrate
d: decomposition
C₃H₅: cyclopropyl

EXAMPLES 57–94

Treatment in the same manner as in Example 1 or 9 gives the following compounds:

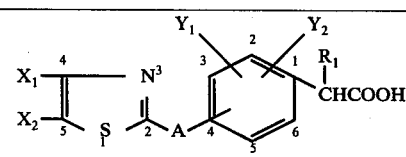

| Ex. No. | $X_1$ | $X_2$ | A | $Y_1$ | $Y_2$ | * | $R_1$ | mp (°C) |
|---|---|---|---|---|---|---|---|---|
| 57 | H | H | O | H | H | 4 | H | 150–151 |
| 58 | H | H | O | H | H | 3 | CH₃ | 88–89 |
| 59 | CH₃ | CH₃ | O | H | H | 4 | " | 122–124 |
| 60 | CH₃ | H | O | H | H | 4 | " | 87–88 Ca.H₂O 175(d) |
| 61 | H | H | O | 3-OCH₃ | H | 4 | " | 93–94 |
| 62 | H | H | O | 3-CH₃ | H | 4 | " | 120–121 |
| 63 | H | H | O | 2-CH₃ | H | 4 | " | 86–87 |
| 64 | H | H | O | 2-Cl | H | 4 | " | 115–116 |
| 65 | H | H | O | 3-Cl | H | 4 | " | 74–75 |
| 66 | H | H | O | 2-F | H | 4 | " | |

-continued

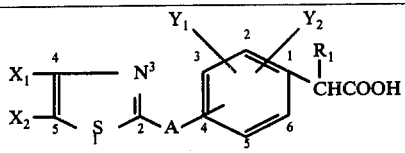

| Ex. No. | $X_1$ | $X_2$ | A | $Y_1$ | $Y_2$ | * | $R_1$ | mp (°C) |
|---|---|---|---|---|---|---|---|---|
| 67 | H | H | O | 3-F | H | 4 | " | 107–108 |
| 68 | H | H | O | 2-Cl | 3-CH$_3$ | 4 | " | 147–148 |
| 69 | H | H | O | 2-CH$_3$ | 5-Cl | 4 | " | 130–131 |
| 70 | H | H | O | H | H | 4 | C$_2$H$_5$ | 115–116 |
| 71 | H | H | O | H | H | 4 | CH$_2$—CH=CH$_2$ | Ca.H$_2$O 134(d) |
| 72 | H | H | O | H | H | 4 | CH$_2$—C≡CH | 99–100 |
| 73 | H | H | O | H | H | 4 | CH$_2$—C$_3$H$_5$ | 85–86 |
| 74 | H | H | O | H | H | 4 | CH$_2$—ĊCH$_3$=CH$_2$ | 111–112 |
| 75 | H | H | O | H | H | 4 | CH$_2$—C$_6$H$_5$ | 121–122 |
| 76 | H | H | NH | H | H | 4 | H | 195–196 |
| 77 | H | H | NH | 3-Cl | H | 4 | CH$_3$ | 144–145 |
| 78 | H | H | NH | 2-F | H | 4 | " | 190–191.5 |
| 79 | H | H | NH | 3-Cl | 5-Cl | 4 | " | 177–178 |
| 80 | CH$_3$ | H | NH | 2-Cl | H | 4 | " | 185–188 |
| 81 | CH$_3$ | H | NH | 3-F | H | 4 | " | 163–164 |
| 82 | CH$_3$ | H | NH | 2-F | H | 4 | " | 202–204 |
| 83 | CH$_3$ | H | NH | 3-CH$_3$ | H | 4 | " | 201–202 |
| 84 | H | H | NH | 2-Cl | H | 4 | " | 174–175 |
| 85 | H | H | NH | 2-CH$_3$ | H | 4 | " | 160–161.5 |
| 86 | H | H | N—CH$_3$ | H | H | 4 | H | 202–204 |
| 87 | H | H | N—CH$_3$ | 2-Cl | H | 4 | CH$_3$ | 141–142 |
| 88 | H | H | N—CH$_3$ | 3-Cl | 5-Cl | 4 | " | 180–181 |
| 89 | H | H | N—CH$_3$ | 2-F | H | 4 | CH$_3$ | 111–112.5 |
| 90 | CH$_3$ | H | N—CH$_3$ | 3-Cl | 5-Cl | 4 | " | 138–139 |
| 91 | H | H | N—CH$_3$ | 2-CH$_3$ | H | 4 | " | 165–166 |
| 92 | H | H | N—CH$_3$ | 3-F | H | 4 | " | 98–100 |
| 93 | H | H | N—CH$_2$—CH=CH$_2$ | H | H | 4 | H | 139–140 |
| 94 | H | H | N—CH$_2$—CH=CH$_2$ | H | H | 4 | CH$_3$ | 118–119 |

*The position of the benzene ring substituted by thiazole-A- group.
Other abbreviations have the same meanings described above.

What is claimed is:

1. A compound of the formula:

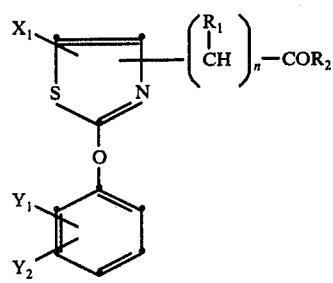

wherein $R_1$ is hydrogen, $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_2$ is hydroxy, $C_{1-5}$ alkoxy or OM, wherein M is alkali metal, or one equivalent of alkaline earth metal, cupric or aluminium cation; $n$ is an integer of 0 or 1; $X_1$ is hydrogen or $C_{1-5}$ alkyl, and $Y_1$ and $Y_2$ are independently hydrogen, halogen, $C_{1-5}$ alkyl, $C_{1-5}$ alkoxy or trifluoromethyl.

2. A compound of the formula:

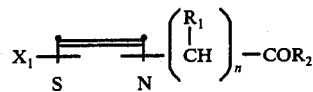

wherein $R_1$ is hydrogen, $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_2$ is hydroxy, $C_{1-5}$ alkoxy or OM, wherein M is alkali metal, or one equivalent of alkaline earth metal cupric or aluminium cation; $n$ is an integer of 0 or 1; $X_1$ is hydrogen or $C_{1-5}$ alkyl, and $Y_1$ and $Y_2$ are independently hydrogen, halogen, $C_{1-5}$ alkyl, $C_{1-5}$ alkoxy or trifluoromethyl.

3. A compound of the formula:

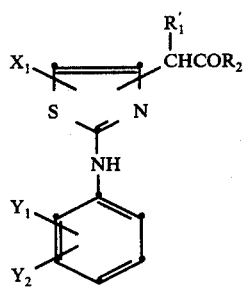

wherein $R_1'$ is $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_2$ is hydroxy, $C_{1-5}$ alkoxy or OM, wherein M is alkali metal, or one equivalent of alkaline earth metal, cupric or aluminium cation; $X_1$ is hydrogen or $C_{1-5}$ alkyl, and $Y_1$ and $Y_2$ are independently hydrogen, halogen, $C_{1-5}$ alkyl, $C_{1-5}$ alkoxy or trifluoromethyl.

4. A compound of the formula:

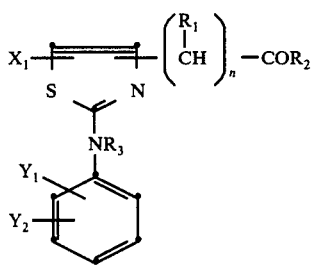

wherein $R_1$ is hydrogen, $C_{1-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $R_2$ is hydroxy, $C_{1-5}$ alkoxy or OM; wherein M is alkali metal, or one equivalent of alkaline earth metal, cupric or aluminium cation; $R_3$ is $C_{1-5}$ alkyl, $C_{2-5}$ alkenyl, $C_{3-5}$ alkyl, $C_{2-5}$ alkenyl, $C_{3-5}$ alkynyl, $C_{3-6}$ cycloalkyl-$C_{1-3}$ alkyl or $C_{7-8}$ aralkyl; $n$ is an integer of 0 or 1; $X_1$ is hydrogen or $C_{1-5}$ alkyl, and $Y_1$ and $Y_2$ are independently hydrogen, halogen, $C_{1-5}$ alkyl, $C_{1-5}$ alkoxy or trifluoromethyl.

5. A compound of claim 1 wherein $X_1$ is hydrogen or methyl; $Y_1$ and $Y_2$ are independently hydrogen, fluorine, chlorine or methyl; $R_1$ is hydrogen or methyl and $n$ is 1.

6. A compound of claim 2 wherein $X_1$ is hydrogen or methyl, both $Y_1$ and $Y_2$ are hydrogen and $R_1$ is hydrogen or methyl.

7. A compound of claim 3 wherein $X_1$ is hydrogen or methyl; both $Y_1$ and $Y_2$ are hydrogen and $R_1'$ is methyl.

8. A compound of claim 4 wherein $X_1$ is hydrogen or methyl; both $Y_1$ and $Y_2$ are hydrogen, $R_1$ is hydrogen or methyl; $R_3$ is methyl and $n$ is 1.

9. A compound according to claim 1, namely 2-(2-phenoxy-4-methyl-5-thiazolyl)propionic acid or a metal salt thereof.

10. A compound according to claim 1, namely 2-(2-phenoxy-5-thiazolyl)propionic acid or a metal salt thereof.

11. A compound according to claim 2, namely 2-(2-phenylthio-4-methyl-5-thiazolyl)acetic acid or a metal salt thereof.

12. A compound according to claim 5, namely 2-(2-anilino-4-methyl-5-thiazolyl)propionic acid or a metal salt thereof.

13. A compound according to claim 4, namely 2-[2-(N-methylanilino)-4-thiazolyl]propionic acid or a metal salt thereof.

* * * * *